Figure 1:
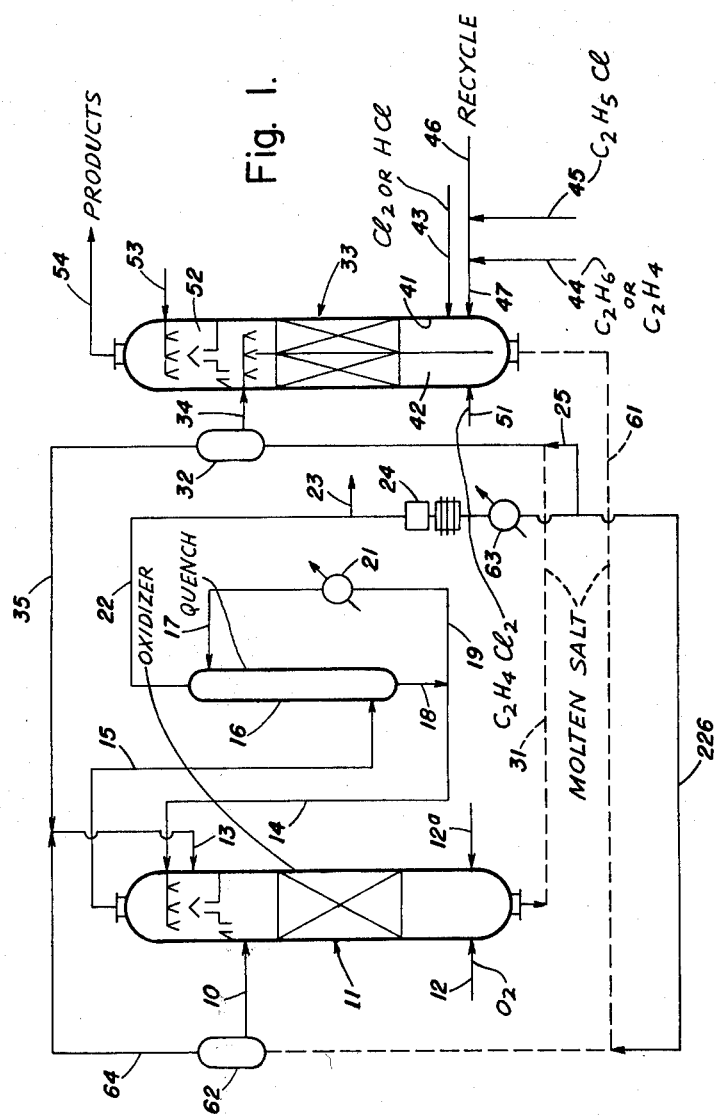

United States Patent [19]

Tsao

[11] 3,963,584
[45] June 15, 1976

[54] RECOVERY OF 1,2-DICHLOROETHANE FROM VINYL CHLORIDE PRODUCTION EFFLUENT

[75] Inventor: Utah Tsao, Jersey City, N.J.

[73] Assignee: The Lummus Company, Bloomfield, N.J.

[22] Filed: Aug. 16, 1974

[21] Appl. No.: 498,081

[52] U.S. Cl. .................................. 203/49; 55/71; 203/70; 260/656 R; 260/654 S; 260/652 P
[51] Int. Cl.² .................................. B01D 3/34
[58] Field of Search ............... 203/49, 67, 68, 70; 55/36, 83, 84, 89, 71; 260/656 R, 654 S, 652 P

[56] References Cited
UNITED STATES PATENTS

| | | |
|---|---|---|
| 3,197,941 | 8/1965 | Colton et al. .................... 55/71 |
| 3,206,524 | 9/1965 | Plaster .............................. 203/70 |
| 3,356,749 | 12/1967 | Van Dijk ........................ 260/654 S |
| 3,409,515 | 11/1968 | Baird et al. ...................... 203/49 |

Primary Examiner—Bernard Nozick
Assistant Examiner—Frank Sever
Attorney, Agent, or Firm—Marn & Jangarathis

[57] ABSTRACT

An effluent from a process for producing vinyl chloride includes 1,2-dichloroethane and heavier components, with the 1,2-dichloroethane being recovered, in a heavy ends stripping column by use of ethane and/or ethylene as stripping gas. The stripping gas is ultimately used for production of vinyl chloride.

3 Claims, 2 Drawing Figures

RECOVERY OF 1,2-DICHLOROETHANE FROM VINYL CHLORIDE PRODUCTION EFFLUENT

This invention relates to the production of vinyl chloride, and more particularly to a new and improved process for recovering chlorinated hydrocarbons from an effluent produced in a process directed to the production of vinyl chloride.

In a process for producing vinyl chloride, the effluent includes 1,2-dichloroethane and higher boiling chlorinated hydrocarbons. The 1,2-dichloroethane is generally separated from the higher boiling chlorinated hydrocarbons in a heavy ends distillation column in which 1,2-dichloroethane is recovered as overhead. In most cases, the bottoms from the heavy ends column includes varying amounts of 1,2-dichloroethane and as a result, various processes have been proposed for further treating the bottoms from the heavy ends distillation column in order to recover 1,2-dichloroethane therefrom; e.g., U.S. Pat. No. 3,634,200. The necessity to provide for further treatment of the bottoms from the heavy ends column to maximize recovery of 1,2-dichloroethane adds to the capital and operating expense of the plant and, accordingly, there is a need for improved methods for recovering 1,2-dichloroethane from higher boiling (heavier)components.

Accordingly, the principle object of the present invention is to provide a new and improved process for recovering 1,2-dichloroethane from heavier materials produced in a process directed to the production of vinyl chloride.

In accordance with the present invention, there is provided a process for producing vinyl chloride wherein ethane and/or ethylene are chlorinated to produce a reaction effluent containing vinyl chloride, 1,2-dichloroethane and chlorinated hydrocarbons heavier than 1,2-dichloroethane. Vinyl chloride is recovered from the effluent and 1,2-dichloroethane is stripped from the heavier chlorinated hydrocarbons by use of a stripping gas which contains ethane and/or ethylene, with the stripped 1,2-dichloroethane being dehydrochlorinated to vinyl chloride. The invention will be further described with respect to the preferred embodiment in which a molten salt is employed for the chlorination of ethane and/or ethylene, but as hereinafter described, the broader aspects of the present invention are not limited to such a preferred technique.

More particularly ethane and/or ethylene is contacted with a melt comprising a multivalent metal chloride in its higher and lower valence state, either with or without hydrogen chloride and/or chlorine as a chlorinating agent, preferably with chlorine and/or hydrogen chloride, to produce a reaction effluent comprising vinyl chloride, 1,2-dichloroethane and chlorinated hydrocarbons heavier than 1,2-dichloroethane. As hereinafter described, the reaction effluent may also include other components such as ethyl chloride, ethane, ethylene, etc.

The reaction effluent is then introduced into a separation and recovery section wherein components lighter (lower boiling) than 1,2-dichloroethane are separated from the effluent; i.e., vinyl chloride, ethyl chloride, ethane, ethylene. The remaining effluent contains 1,2-dichlorethane and chlorinated hydrocarbons heavier than 1,2-dichloroethane (higher boiling than 1,2-dichloroethane) which may be one or more of the following: trichloroethane, tetrachloroethane, tetrachloroethylene, or trichloroethylene. The heavier components may further include chlorinated butanes and/or butenes and tars. In accordance with the present invention, the stream containing 1,2-dichloroethane and heavier chlorinated hydrocarbons is introduced into a stripping zone wherein 1,2-dichloroethane is stripped therefrom by use of a stripping gas containing ethane, ethylene or mixtures thereof. The ethane and/or ethylene used in the stripping gas may be fresh feed or, hereinafter described, the ethane and/or ethylene may be a recycle gas from the process. It is also to be understood that the stripping gas can include components in addition to ethane and/or ethylene; in particular an inert gas, such as nitrogen.

The stripper for stripping 1,2-dichloroethane from heavier components is operated at temperatures and pressures which are effective for separating 1,2-dichloroethane from the heavier components. In general, the stripper is operated at an overhead temperature from about 225° to about 350°F, preferably an overhead temperature from about 280° to about 310°F, a bottoms temperature from about 270° to about 410°F, preferably from about 325° to about 360°F and a pressure from about 20 psig to about 130 psig, preferably from about 55 psig to about 80 psig.

The stripping gas is preferably introduced into the bottoms reboiler of the stripper, whereby the partial pressure of 1,2-dichloroethane over the heavy residue is reduced and the stripping gas is heated. The stripping gas is preferably introduced in an amount to provide a mole ratio of stripping gas to vapor generated in the bottoms reboiler of from 0.5:1 to 1.5:1.

The 1,2-dichloroethane stream recovered from the stripper, which also includes ethane and/or ethylene used as stripping gas, is then introduced into a dehydrochlorination reaction zone to effect dehydrochlorination of 1,2-dichloroethane to vinyl chloride. The dehydrochlorination may be effected by a conventional thermal or catalytic process or by the use, as hereinafter described, of a molten salt mixture containing the higher and lower valent forms of a multivalent metal chloride. The dehydrochlorination reaction effluent is then introduced into a separation and recovery zone for recovery of the various components.

Accordingly, in accordance with the present invention, separation of 1,2-dichloroethane from heavier components is maximized by using ethane and/or ethylene as a stripping gas. The recovered 1,2-dichloroethane overhead, which includes the stripping gas, is subjected to dehydrochlorination. The ethane and/or ethylene used as stripping gas may be partially chlorinated in the dehydrochlorination zone, as hereinafter described, and in any event, the ethane and/or ethylene or chlorinated product(s) produced therefrom are ultimately utilized in the production of vinyl chloride.

As hereinabove noted the melts employed in the chlorination include the higher and lower valent forms of a chloride of a multivalent metal; i.e., a metal having more than one positive valence state, such as manganese, iron copper, cobalt and chromium, preferably copper. In the cases of higher melting multivalent metal chlorides, such as copper chlorides, a metal salt melting point depressant which is non-volatile and resistant to the action of oxygen at the process conditions, such as a chloride of a univalent metal, i.e., a metal having only one positive valence state, is added to the multivalent metal chloride to form a molten salt mixture having a reduced melting point. The univalent metal chlorides, are preferably alkali metal chlorides, such as potassium and lithium chlorides in particular, but it is to be understood that other metal chlorides and mixtures thereof, such as the heavy metal chlorides, i.e., heavier than copper, of Groups I, II, III and IV of the Periodic Table; e.g., zinc, silver, and thallium chloride, may also be employed. The metal chloride melting point depressant is added in an amount sufficient to maintain the salt mixture as a melt at the reaction temperatures, and is generally added in an amount sufficient to adjust the melting point of the molten salt mixture to a temperature of below about 500°F. In the case of a salt mixture of copper chlorides and potassium chloride, the composition of the melt ranges between about 20 and about 40%, preferably about 30%, by weight, potassium chloride, with the remaining being copper chlorides. It is to be understood, however, that in some cases the catalyst melt may have a melting point higher 500°F., provided the catalyst remains in the form of the melt throughout the processing steps. It is further to be understood that the melt may contain a mixture of multivalent metal chlorides or other reaction promoters. It is also to be understood that in some cases, metal chloride may be maintained as a melt without the addition of a univalent metal halide.

The chlorination reaction sequence for converting ethane and/or ethylene to vinyl chloride, using copper chloride as a representative example, is believed to be represented by the following equations:

(1) $2CuCl_2 \rightarrow 2CuCl + Cl_2$ (2) $C_2H_6 + Cl_2 \rightarrow C_2H_5Cl + HCl$ (3) $C_2H_4 + Cl_2 \rightarrow C_2H_4Cl_2$ (4) $C_2H_4Cl_2 \rightarrow C_2H_3Cl + HCl$ (5) $C_2H_5Cl \rightarrow C_2H_4Cl_2 + HCl$ (6) $C_2H_5Cl + Cl_2 \rightarrow C_2H_4Cl_2 + HCl$ (7) $C_2H_4Cl_2 \rightarrow C_2H_3Cl + HCl$ It should be apparent from the hereinabove described reaction sequence, as represented by the above equations, that there is a continuous depletion of the higher valent metal chloride; i.e., cupric chloride, and a net production of hydrogen chloride. Therefore, if the process is to be effected on a continuous basis, a provision must be made for regeneration of the cupric chloride and disposal of the hydrogen chloride.

In accordance with the preferred embodiment of the invention, the melt containing the multivalent metal chloride, in both its higher and lower valence state, may be initially contacted in a separate reaction zone with an oxygen-containing gas to produce the oxychloride of the metal, and the melt, now also containing the oxychloride of the multivalent metal, is then contacted in a chlorination zone with chlorine and/or hydrogen chloride and the feed containing ethane and/or ethylene to produce vinyl chloride and dichloroethane. The reaction between the melt and the oxygen-containing gas, using copper chloride as a representative multivalent metal chloride, is represented by the following equation:

(8) $2CuCl + \frac{1}{2}O_2 \rightarrow CuO \cdot CuCl_2$

The copper oxychloride then reacts with the hydrogen chloride generated during the production of the vinyl chloride as represented by the following equation:

(9) $CuO \cdot CuCl_2 + 2HCl \rightarrow 2CuCl_2 + H_2O$

Thus, in accordance with this embodiment, there is no net production of hydrogen chloride and no net depletion of cupric chloride, and in fact, in order to operate the process on a continuous basis, chlorine and/or hydrogen chloride must be added to the system as represented by the following overall equations:

(10) $C_2H_6 + \frac{1}{2}Cl_2 + \frac{3}{4}O_2 \rightarrow C_2H_3Cl + 3/2\ H_2O$

(11) $C_2H_6 + HCl + O_2 \rightarrow C_2H_3Cl + 2\ H_2O$

(12) $C_2H_4 + \frac{1}{2}Cl_2 + \frac{1}{4}O_2 \rightarrow C_2H_3Cl + \frac{1}{2}\ H_2O$

(13) $C_2H_4 + HCl + \frac{1}{2}O_2 \rightarrow C_2H_3Cl + H_2O$

The hydrogen chloride and/or chlorine may be added to the system either with the oxygen containing gas or in the chlorination zone with the ethane and/or ethylene feed, preferably with the ethane and/or ethylene feed so as to eliminate the necessity of providing means for recovering hydrogen chloride and/or chlorine from the gaseous effluent from the oxygen-contacting step. In addition, the additions of chlorine and/or hydrogen chloride with the ethane and/or ethylene feed improves the yield of vinyl chloride.

In accordance with another embodiment of the invention, the oxygen containing gas may be introduced into the chlorination zone with the ethane and/or ethylene feed to produce the oxychloride of the multivalent metal, in situ, but such a procedure is not preferred in that there may be a loss of ethane and/or ethylene feed by combustion. In addition, the quantities of oxygen and ethane and/or ethylene would have to be regulated to prevent explosive compositions.

In accordance with a further embodiment of the invention, the higher valent metal chloride may be regenerated by contacting the melt with a chlorine-containing gas, such contacting being effected either simultaneously with the production of vinyl chloride and dichloroethane from the ethane and/or ethylene feed or in a separate reaction zone. The regeneration of the higher valent multivalent metal chloride, using copper chloride as a representative example, may be represented by the following equation:

(14) $2CuCl + Cl_2 \rightarrow 2CuCl_2$ and the overall reaction, using ethylene as a representative feed, by the following equation:

(15) $C_2H_4 + Cl_2 \rightarrow C_2H_3Cl + HCl$

This procedure is not particularly preferred in that there is a net production of hydrogen chloride.

In accordance with still another embodiment of the invention, the hydrogen chloride generated during the production of vinyl chloride and dichloroethane in the chlorination zone may be recovered from the reaction effluent, and employed in a separate reaction zone, along with an oxygen-containing gas, to regenerate the higher valent metal chloride, as represented by the following equation:

(16) $2HCl + 2CuCl + \frac{1}{2}O_2 \rightarrow 2CuCl_2 + H_2O$

This procedure is also less preferred in that provision must be made for recovering the hydrogen chloride from the chlorination zone reaction effluent.

Although several embodiments for the chlorination of ethane and/or ethylene by the use of melts containing a multivalent metal chloride in both its higher and lower valence state have been described, the preferred embodiment for such chlorination involves contacting of the melt with molecular oxygen in a first reaction zone to provide a molten salt mixture which further includes the oxychloride of the multivalent metal, followed by circulating the melt from the first reaction zone to a second reaction zone (chlorination zone) wherein the melt is contacted with ethane and/or ethylene and chlorine and/or hydrogen chloride to produce a chlorinated effluent, including vinyl chloride and dichloroethane. This embodiment is preferred in that higher yields are obtained with the direct addition of chlorine and/or hydrogen chloride into the chlorination reactor.

The reaction effluent produced in the chlorination reactor is introduced into a separation and recovery zone wherein vinyl chloride is recovered, as reaction product, and wherein 1,2-dichloroethane is stripped from heavier components using a stripping gas which contains ethane and/or ethylene. The stripped 1,2-dichloroethane which also includes ethane and/or ethylene, used as stripping gas, is then dehydrochlorinated to vinyl chloride.

In accordance with one embodiment, the dichloroethane is dehydrochlorinated to vinyl chloride by contacting the dichloroethane with a melt containing a multivalent metal chloride in both its higher and lower valence state, with the reaction being represented by the hereinabove equation (7):

(7) $C_2H_4Cl_2 \rightarrow C_2H_3Cl + HCl$ 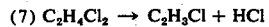

The melt may also contain the oxychloride of the multivalent metal whereby there is essentially no net production of hydrogen chloride, as represented by hereinabove equation (9):

(9) $2HCl + CuO \cdot CuCl_2 \rightarrow 2CuCl_2 + H_2O$ 

The use of the hereinabove described melts for the dehydrochlorination of dichloroethane (in particular the 1,2-dichloroethane) to vinyl chloride is particularly advantageous in that the melts direct the dehydrochlorination to the production of vinyl chloride at high rates of conversion and high vinyl chloride selectivity. The 1,2-dichloroethane, which constitutes the major portions of the dichloroethane produced (in some cases essentially all of the dichloroethane product is 1,2-dichloroethane), may be converted to vinyl chloride at conversion rates greater than 90%, while retaining vinyl chloride selectivity at greater than 90%. It is to be understood, however, that although the dehydrochlorination of the present invention may be effectively operated at conversions greater than 90%, for some operations, lower conversion rates may be employed. The ethane and/or ethylene introduced into the dehydrochlorination zone, as a result of the chlorinating ability of the melt, may be converted, in part or in total, to chlorinated product, as described with reference to the chlorination zone (equations 1-7). The chlorinated products produced from the ethane and/or ethylene or the ethane and/or ethylene, itself is utilized for the production of vinyl chloride by recycle of various components as hereinabove described.

The dichloroethane (primarily 1,2-dichloroethane) may also be dehydrochlorinated to vinyl chloride at dehydrochlorination temperatures and pressures by any of the other procedures known in the art. Thus, for example, the dichloroethane may be either thermally or catalytically cracked to vinyl chloride as known in the art. The use of such procedures is well-known in the art and, accordingly, no further description thereof is deemed necessary for a full understanding of the invention. In general, in such a system the ethane and/or ethylene is unchanged in passage through the dehydrochlorination zone.

The chlorination and dehydrochlorination in the presence of a melt are generally operated at temperatures from about 700° to about 1200°F., preferably from about 750° to about 1000°F., although the temperatures may be as low as 575°F., and at pressures from about 1 to about 20 atmospheres. The contacting of the feed and melt is generally effected in a countercurrent fashion preferably with the feed as a continuous vapor phase, at residence times from about 1 to about 60 seconds although longer residence times may be employed. In the embodiments of the invention wherein the melt is previously contacted with oxygen, in a separate reaction zone, such contacting is generally effected at temperatures from about 600° to about 900°F., although higher temperatures may be employed. The preferred operating temperatures for the oxidation of the melt are from about 750° to about 870°F.

It should be apparent from the hereinabove noted reaction sequences, that the melt containing the multivalent metal chloride in some cases, participates in the reaction sequence and accordingly, does not behave only as a catalyst. Thus, for example, in the preferred embodiments of the invention, the melt functions to transfer oxygen, and as should be apparent from hereinabove noted equations, sufficient oxychloride must be produced to provide the oxygen requirements for the reactions, such requirements being greater for ethane as compared to ethylene and greater for hydrogen chloride as compared to chlorine. In general, the oxychloride content of the molten mixture introduced into the chlorination reactor ranges from about 0.5 to about 5.5% and preferably from about 1 to about 3%, all by weight, of the melt.

The melt, in addition to functioning as a reactant and/or catalyst is a temperature regulator. Thus, the circulating melt has a high heat absorption capacity, thereby preventing runaway reaction during the exothermic chlorination and oxygen-contacting steps. The absorbed heat of reaction may be employed to both heat the various reactants to reaction temperature and supply heat for the endothermic dehydrochlorination. It should be apparent, however, that if additional heating or cooling is required such heating or cooling may be supplied from an external source. It should also be apparent that the heat absorption capacity of the melt functions to limit temperature variations, i.e., temperature gradients, during the reactions.

Thus, as should be apparent from the hereinabove description of the present invention, vinyl chloride and dichloroethane may be produced from ethane and/or ethylene by contacting thereof with a melt containing a multivalent metal chloride in both its higher ane lower valence state, in the absence or presence of chlorine and/or hydrogen chloride, and in the absence or presence of the corresponding oxychloride, preferably in the presence of chlorine and/or hydrogen chloride and in the presence of the oxychloride. The 1,2-dichloroethane produced in the chlorination is separated from heavier chlorinated components by use of a stripping gas containing ethane and/or ethylene with the stripped 1,2-dichloroethane, including ethane and/or ethylene, being dehydrochlorinated to vinyl chloride, preferably by direct contact with a melt containing a multivalent metal chloride in its higher and lower valence state. The ethane and/or ethylene used as stripping gas is also employed for the ultimate production of vinyl chloride. The chlorination and dehydrochlorination as hereinafter described, are preferably effected by using the same circulating melt, but it should be readily apparent that each of the two steps could be effected with molten mixtures having different multivalent metal chlorides. Similarly, melts of identical compositions could be employed in each of the steps, without circulating such identical melts between the two steps.

In accordance with a preferred embodiment of the invention, vinyl chloride is produced from a net feed of ethane, molecular oxygen and chlorine and/or hydrogen chloride, using copper chlorides as the molten salt mixture, with the intermediate products produced during the reaction being effectively converted to vinyl chloride. In accordance with this preferred embodiment, the use of ethane or a mixture of ethylene and ethane, as a stripping gas, for stripping 1,2-dichloroethane from heavier components improves the overall process.

The molten salt mixture, preferably containing from about 20 to about 40% potassium chloride, as a melting point depressant, with the remainder being copper chlorides, all by weight, is contacted in a first reaction zone with molecular oxygen to produce copper oxychloride. The cupric chloride content of the melt is generally at least about 16%, by weight, of the melt, and generally from about 18% to about 50%, by weight, in order to provide sufficient cupric chloride for the subsequent chlorination and dehydrochlorination reactions. It is to be understood, however, that lower amounts of cupric chloride may also be employed by increasing salt circulation rates and residence tims. As a result of the various reactions which occur during the chlorination and dehydrochlorination steps, the cupric chloride content of the melt does not significantly vary through the various reactions zones. The molecular oxygen is preferably introduced in an amount, and at a rate, to provide a molten salt mixture containing from about 0.5 to about 5.5%, preferably from about 1 to about 3%, all by weight, of copper oxychloride. It is to be understood that minor amounts of chlorine and/or hydrogen chloride could also be introduced into the first reaction zone, but in accordance with this preferred embodiment, the major portion of the chlorine and/or hydrogen chloride is added to the chlorination zone.

The molten salt mixture, now containing copper oxychloride, is circulated to a second reaction zone (chlorination zone) wherein the molten salt is contacted with ethane and chlorine and/or hydrogen chloride as fresh feed and recycle ethyl chloride. The recycle may also include unconverted ethane and ethylene reaction intermediate. The recycle, as hereinaftter described, may also include 1,1-dichloroethane. The chlorine, if used, is added in amounts which approximate stoichiometric quantities in order to eliminate the presence of chlorine in the reaction effluent, thereby also eliminating the necessity for chlorine recovery and recycle. The reactions which occur in the chlorination zone are believed to be best represented by hereinabove equation (1)–(7) and (9). Thus, fresh ethane and chlorine and/or hydrogen chloride feed are converted to ethyl chloride, ethylene, dichloroethane (both 1,1-dichloroethane and 1,2-dichloroethane, primarily 1,2-dichloroethane) and vinyl chloride, with the recycle ethyl chloride, ethylene, (if any), 1,1-dichloroethane also being ultimately converted to vinyl chloride. The hydrogen chloride generated, in situ, reacts with the copper oxychloride of the melt to produce cupric chloride. In most cases, 100% conversion of the generated hydrogen chloride is not achieved and, accordingly, the reaction effluent may also include some hydrogen chloride. The chlorination reaction effluent withdrawn from the chlorination zone includes, in addition to unconverted ethane, ethylene, ethyl chloride, dichloroethane, dichloroethylene, hydrogen chloride (if any) water vapor and vinyl chloride. The chlorination reaction effluent further includes minor portions of one or more of the following: trichloroethylene, tetrachloroethylene, trichloroethanes, and tetrachloroethanes.

The chlorination reaction effluent is passed to a separation and recovery zone wherein ethane and ethylene are recovered as a light stream, vinyl chloride is recovered as product, ethyl chloride is recovered as recycle for the chlorination zone. A stream comprised of 1,2-dichloroethane and heavier chlorinated hydrocarbons is then introduced into a stripping zone to strip the 1,2-dichloroethane from the heavier hydrocarbons, using as a stripping gas, either a portion of the ethane to be used as fresh feed or all or a portion of the mixture of ethane and ethylene recovered from the chlorination effluent. The mixed ethane-ethylene stream, recovered from the effluent and not used as stripping gas is recycled to the chlorination zone.

In general, the chlorination reaction effluent also includes 1,1-dichloroethane, which is preferably recovered separately from the 1,2-dichloroethane, i.e, with the ethyl chloride, and recycle to the chlorination zone for dehydrochlorination to vinyl chloride. It is to be understood, however, that the 1,1-dichloroethane could be recovered with the 1,2-dichloroethane overhead in the heavy ends column and dehydrochlorinated with the 1,2-dichloroethane in the separate dehydrochlorination zone.

The 1,2-dichloroethane, including ethane or a mixture of ethane and ethylene is introduced into the dehydrochlorination zone and contacted therein with the molten salt from either the first reaction zone, the second reaction zone (chlorination zone), or molten salt from both zones, preferably from the first reaction zone whereby the melt includes oxychloride, to effect dehydrochlorination of the 1,2-dichloroethane to vinyl chloride. The reaction effluent includes vinyl chloride, any unconverted 1,2-dichloroethane, and chlorinated hydrocarbons produced from the ethane or mixture of ethane and ethylene introduced with the 1,2-dichloroethane. In addition, if the melt employed in the dehydrochlorination zone is obtained from the second reaction zone, the dehydrochlorination reaction effluent includes hydrogen chloride, and if the melt is obtained from the first reaction zone, the effluent includes water vapor and any hydrogen chloride which does not react with the copper oxychloride present in the melt. The dehydrochlorination reaction effluent is introduced into a separation and recovery zone to recover the various components, with vinyl chloride being recovered as reaction product, hydrogen chloride, if any, being recycled to the chlorination zone, and unconverted 1,2-dichloroethane being recycled to the dehydrochlorination zone.

The heavier chlorinated hydrocarbons separated from 1,2-dichloroethane are preferably burned to recover chlorine values which are recycled to the melt oxidation zone.

The molten salt to feed weight ratio (based on total feed to the chlorination reaction zone) is preferably from about 25:1 to about 200:1, with the molten salt, at such high salt circulation rates, acting as a heat sink, whereby there is little temperature variation between the various zones; i.e., in general the temperature fluctuation between the various zones is no greater than about 130°F. and generally from about 15° to about 50°F.

It should be readily apparent that in accordance with the preferred embodiment, vinyl chloride is effectively produced from ethane, chlorine and/or hydrogen chloride and oxygen as a result of the recycle of essentially all reaction intermediates, with the overall reaction being represented by equations (10) and/or (11).

It is also to be understood that the preferred ethane feed could also contain some ethylene, and/or propane and/or methane as for example, in the case where a $C_2$ stream is recovered from a refinery.

Figure 2:
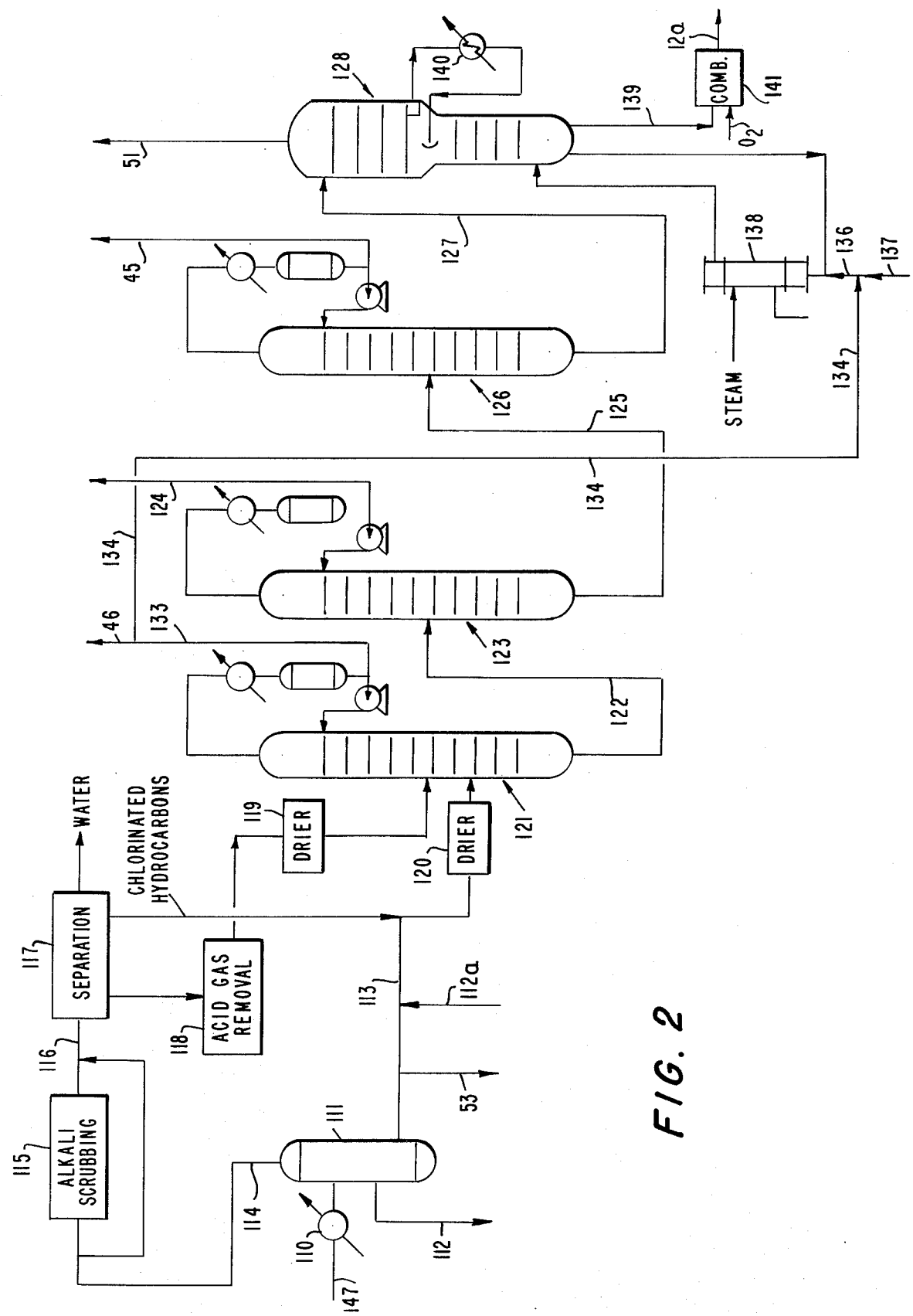

The invention will now be further described with reference to embodiments thereof illustrated in the accompanying drawings wherein:

FIG. 1 is a simplified schematic process flow diagram of the reaction portion of an embodiment of the invention; and FIG. 2 is a simplified schematic process flow diagram of the separation and recovery portion for recovery reaction products.

It is to be understood that the molten copper chloride salts are highly corrosive and, accordingly, the processing equipment must be suitably protected; e.g., the reactors may be lined with ceramic. Similarly, if pumps are used for transporting the molten salts they must also be protected. The molten salts, however, are preferably transferred between the reactors and by the use of gas lifts, as known in the art.

Referring now to FIG. 1, a molten chloride salt, such as a mixture of potassium chloride, cuprous chloride and cupric chloride in line 10 is introduced into the top of the reaction portion of an oxidation vessel 11 maintained, as hereinabove described, at temperatures and pressure suitable for oxidizing the molten salts. A compressed oxygen-containing gas, such as air, in line 12 is introduced into the bottom of vessel 11 and is passed in countercurrent contact to the descending molten salt, resulting in oxidation of the salt to produce copper oxychloride with the concurrent evolution of heat. In addition, a combustion effluent resulting from the combustion of heavier chlorinated by products, such as tri- and tetrachloroethanes and ethylenes and including hydrogen chloride and/or chlorine is introduced into vessel 11 through line 12a, as described in British patent and specification No. 1,205,831.

An effluent gas, comprised essentially of the nitrogen introduced with the air, (the effluent would also include combustion products, if a combustion effluent is introduced through line 12a) rises into the top of the vessel 11 wherein the effluent gas is combined with lift gas, as hereinafter described, introduced through line 13. The effluent gas is directly contacted in the top of vessel 11 with a spray of quench liquid, in particular aqueous hydrogen chloride introduced through line 14 to cool the effluent gas and thereby eliminate any vaporized and entrained salts therefrom. The effluent gas, now containing vaporized quench liquid, is withdrawn from vessel 11 through line 15 and introduced into a direct contact quench tower 16, of a type known in the art wherein the effluent gas is cooled by direct contact with a suitable quench liquid, in particular aqueous hydrogen chloride, introduced through line 17 to thereby remove vaporized quench liquid from the effluent gas.

The quench liquid is withdrawn from the bottom of tower 16 through line 18 and a first portion passed through line 14 for quenching the effluent gas in vessel 11. A second portion of the quench liquid is passed through line 19, containing a cooler 21, for introduction into the quench tower 16 through 17.

An effluent gas, comprised essentially of nitrogen, is withdrawn from quench tower 16 through line 22 and a portion thereof purged through line 23. The remaining portion of the nitrogen effluent gas is compressed in compressor 24 and the temperature thereof regulated in heat exchanger 63 prior to passage through lines 25 and 26 for use as a lift gas for transporting molten salt, as hereinafter described.

The molten salt, now containing copper oxychloride, is withdrawn from the bottom of vessel 11 through line 31 and lifted by the lift gas in line 25 into a separation vessel 32 positioned adjacent the top of the reaction portion of a reaction vessel 33. In separator 32, the molten salt is separated from the lift gas, witht the separated lift gas being withdrawn through line 35 and combined with lift gas from the oxidation reactor for introduction into the quenching portion of vessel 11 through line 13.

The reaction vessel 33 is divided into two separate reaction sections, 41 and 42 with reaction section 41 functioning as a chlorination reaction zone and section 42 as a dehydrochlorination reaction zone. The molten salt, containing cuprous chloride, cupric chloride, copper oxychloride and the potassium chloride melting point depressant, from separator 32, in line 34, is introduced into both reaction sections 41 and 42.

Fresh feed chlorine and/or hydrogen chloride is introduced into the bottom of section 41 through 43 and all or a portion of fresh feed ethane and/or ethylene, preferably ethane, in line 44 is combined with a recycle chlorinated hydrocarbon stream comprised of ethyl chloride and also some dichloroethylene and 1,1-dichloroethane, in line 45, and recycle ethane and ethylene (if any) in line 46, for introduction into the bottom of section 41 through line 47. It is to be understood that the various streams could be separately introduced.

The reaction section 41 is operated at the temperatures and pressures hereinabove described, to produce an effluent which contains, as combined reaction product, vinyl chloride and 1,2-dichloroethane. The effluent also includes ethyl chloride, some 1,1-dichloroethane, dichloroethylenes, ethane, ethylene, water vapor, some hydrogen chloride and heavier chlorinated hydrocarbons.

1,2-dichloroethane, including ethane and/or ethylene in line 51 is introduced into the bottom of reaction section 42 and countercurrently contacts the descending molten salt. As a result of such contact, the 1,2-dichloroethane is dehydrochlorinated to vinyl chloride, and hydrogen chloride, which as hereinabove noted, reacts with the oxychloride present in the melt. In addition, some or all of the ethane and/or ethylene is chlorinated as a result of contact with the melt.

It is to be understood, that the dehydrochlorination reaction may also be effected in a separate vessel instead of in a separate section of vessel 33.

The reaction effluent from chlorination section 41 is combined with the reaction effluent from dehydrochlorination reaction section 42 in quenching section 52 wherein the effluent gas is directly contacted with a spray of quench liquid, in particular one or more of the chlorinated hydrocarbons produced in reaction section 41, introduced through line 53 to cool the effluent gas and thereby eliminate vaporized and entrained salts therefrom.

The effluent gas, now containing vaporized quench liquid, is withdrawn from vessel 33 through line 54 and introduced into a separation and recovery section (FIG. 2) for recovery of the various components.

A molten salt obtained from sections 41 and 42 is withdrawn from the bottom of reactor 33 through line 61 and lifted by lift gas in line 26 into a separation vessel 62 positioned adjacent the top of reactor 11. In separator 62 the molten salt is separated from the lift gas and introduced through line 10 into vessel 11. The lift gas is withdrawn from separator 62 through line 64 and combined with the lift gas in line 35 for introduction into the top quenching section of vessel 11 through line 13.

Referring now to FIG. 2, the reaction effluent in line 54 is cooled in condenser 110, primarily to condense a portion of the water therefrom (the condensed water would also contain hydrogen chloride, if present), the aforesaid cooling also resulting in the condensation of chlorinated hydrocarbons, including the chlorinated hydrocarbons used as quench liquid. The condensed water and chlorinated hydrocarbons are separated in a separator III, with a water phase being withdrawn through line 113. A portion of the chlorinated hydrocarbons in line 113 is recycled through line 53 as quench liquid for reactor 33. Alternatively, all of such chlorinated hydrocarbons, if required, may be recycled as quench liquid. The water phase in line 112 is stripped of entrained and dissolved chlorinated hydrocarbon in a stripping column (not shown) and the recovered chlorinated hydrocarbons (from the stripping column) in line 112a are combined with the chlorinated hydrocarbons in line 113. Depending on the amount of hydrogen chloride present in the water, the water may also be treated to recover hydrogen chloride or a concentrated solution of hydrogen chloride.

The remaining portion of the gaseous effluent in line 114 is optionally passed through an alkali scrubbing zone, of a type known in the art, schematically indicated as 115, to remove any remaining hydrogen chloride therefrom.

The gaseous effluent from the alkali scrubbing zone 115, if used, in line 116 is generally passed through a further cooling and separation zone, schematically indicated as 117, to condense further water and chlorinated hydrocarbons therefrom; an acid gas removal zone 118, of a type known in the art, to remove any acid gas, primarily carbon dioxide, and a drier 119, and introduced into a fractional distillation column 121. The chlorinated hydrocarbons in line 113 and chlorinated hydrocarbons separated in zone 117 are combined and dried in drier 120 for introduction into column 121. Alternatively, if required, a portion of the chlorinated hydrocarbons recovered in zone 117 may be recycled as quench liquid to reactor 33. The water separated in zone 117 may be passed to a stripping column to recover any chlorinated hydrocarbons with such recovered chlorinated hydrocarbons also being introduced into column 121.

The column 121 is operated at temperatures and pressures to produce a gaseous overhead comprised of ethane and ethylene, which is recovered in line 133. All or a portion or none of the ethane-ethylene stream in line 133 may be used as a stripping gas in line 134, with the remainder, if any, being recycled to reactor 33 through line 46.

A chlorinated hydrocarbon bottoms withdrawn from column 121 through line 122 is introduced into a fractional distillation column 123 operated at temperatures and pressures to produced an overhead primarily comprised of vinyl chloride which is recovered through line 124.

A chlorinated hydrocarbon bottoms withdrawn from column 123 through line 125 is introduced into a fractional distillation column 126 operated at temperatures and pressures to recover as overhead 1,1-dichloroethane and lower boiling chlorinated hydrocarbons, in particular ethyl chloride and dichloroethylenes. The overhead from column 126, comprised essentially of 1,1-dichloroethane, dichloroethylenes and ethyl chloride is recovered in line 45 for recycle to reactor 33. If desired, the overhead from column 126 may be further fractionated to produce a recycle stream essentially free of dichloroethylenes. As a further alternative, column 126 may be operated to recover ethyl chloride as overhead in which case any 1,1-dichloroethane and dichloroethylenes will be ultimately recovered with the stripped 1,2-dichloroethane.

A bottoms of 1,2-dichloroethane and heavier chlorinated products is withdrawn from column 126 through line 127 and introduced into the top of stripping column 28. The stripping gas in line 136, which may be either ethane and/or ethylene fresh feed, provided through line 137, or ethane and ethylene recovered from the chlorination effluent in line 134 or a combination of both, is introduced into the bottom reboiler 138 to reduced the partial pressure over the heavy residue in the reboiler and thereby reduce the boiling point of the residue in the reboiler. The stripper is operated, as hereinabove described, to recover 1,2-dichloroethane and ethane and/or ethylene, as overhead product in line 51, for introduction into the dehydrochlorination section 42 of reactor 33. The stripper is also preferably provided with a side reboiler 140.

The bottoms from column 128, comprised of chlorinated hydrocarbons heavier than 1,2-dichloroethane in line 139 is introduced into a combustion zone 141 along with oxygen wherein the chlorinated hydrocarbons are burned to produce a combustion effluent, including the chlorine values of the chlorinated hydrocarbon as chlorine and/or hydrogen chloride. The combustion effluent from combustion zone 141 is introduced into oxidizer 11 through line 12a.

It is to be understood that although the present invention has been described with respect to the preferred embodiment in which ethane and/or ethylene are chlorinated by the use of molten salts the present invention is also applicable to other processes for chlorinating (the term chlorinating is used in a generic sense and also includes so called "oxychlorination" processes) ethane and/or ethylene to produce vinyl chloride; i.e., the heavy ends recovered from such a process including 1,2-dichloroethane and heavier components is introduced into a stripping zone wherein 1,2-dichloroethane is stripped from heavier chlorinated components by use of ethane and/or ethylene (either recycle or fresh feed). Thud, the effluent obtained by the chlorination and/or oxychlorination of ethane and/or ethylene includes 1,2-dichloroethane and heavier components, and 1,2-dichloroethane is separated from such heavier components by the use of ethane and/or ethylene, as a stripping gas, with the stripped 1,2-dichloroethane, including stripping gas, being introduced into a dehydrochlorination reaction zone. The dehydrochlorination effluent is then treated to recover various components whereby the ethane and/or ethylene used stripping gas is eventually employed for the production of vinyl chloride.

The invention will be further described with respect to the following example, but the scope of the invention is not to be limited thereby.

EXAMPLE

The feed in line 127, comprised of 60 weight percent 1,2-dichloroethane is introduced into column 128 at a temperature of 320°F. The column is operated at a pressure of 70 psig, an overhead temperature of 300°F, a bottoms temperature of 275°F and a side reboiler temperature of 340°F. Fresh feed ethane is introduced into the bottoms reboiler to provide a mole ratio of ethane to vapor generated in the reboiler of 1.5:1.

The heavy residue contains no more than 1 weight percent 1,2-dichloroethane.

The present invention is advantageous in that loss of 1,2-dichloroethane in the heavier chlorinated residuum is minimized; i.e., by proceeding in accordance with the present invention the 1,2-dichloroethane content of the heavier chlorinated residuum can be reduced to 1 weight percent and less. Furthermore, the above is effectively accomplished without the introduction of extraneous components into the process, with the stripping gas being ultimately converted to final product.

Numerous modifications and variations of the present invention are possible in light of the above teachings and, therefore, within the scope of the appended claims the invention may be practiced otherwise than as particularly described.

WHAT IS CLAIMED IS:

1. A process for recovering 1,2-dichloroethane from a mixture of 1,2-dichloroethane and at least one chlorinated hydrocarbon heavier than 1,2-dichloroethane selected from the group consisting of trichloroethane, tetrachloroethane, tetrachloroethylene, trichloroethylene, chlorinated butanes and chlorinated butenes, comprising:
   introducing said mixture into a stripping column operated at an overhead temperature from about 225° to about 350°F, a bottoms temperature from about 270° to about 410°F and a pressure from about 20 psig to about 130 psig to separate and recover 1,2-dichloroethane from the mixture as overhead;
   introducing into the bottoms of said stripping column, as stripping gas, a member selected from the group consisting of ethane, ethylene and mixtures of ethane and ethylene to strip 1,2-dichloroethane from said mixture, said stripping gas being introduced in a molar amount sufficient to reduce the partial pressure of 1,2-dichloroethane over the heavier chlorinated hydrocarbons and provide a bottoms containing no greater than 1 wt.% of 1,2-dichloroethane;
   recovering as overhead from said stripping column 1,2-dichloroethane and said stripping gas; and
   recovering a bottoms from the stripping column having a 1,2-dichloroethane content of no greater than 1 wt. %.

2. The process of claim 1 wherein the stripping column includes a bottoms reboiler and the stripping gas is introduced into the bottoms of the stripping column through the bottoms reboiler.

3. The process of claim 1 wherein the stripping gas is employed in an amount to provide a mole ratio of stripping gas to vapor generated in the bottoms reboiler of from 0.5:1 to 1.5:1.

* * * * *

UNITED STATES PATENT OFFICE
CERTIFICATE OF CORRECTION

Patent No. 3,963,584　　　　　　　　　　Dated June 15, 1976

Inventor(s) Utah Tsao

It is certified that error appears in the above-identified patent and that said Letters Patent are hereby corrected as shown below:

In The Specification:

Column 3, line 16, delete "remaining" and insert -- remainder --.
Column 6, line 68, "ane" should be -- and --
Column 7, line 46, "tims" should be -- times --;
　　　　　line 67, "hereinaftter" should be -- hereinafter --.
Column 9, line 40, "for recovery" should be -- for recovering --
Column 10, line 25, "throughline" should be -- through line --;
　　　　　line 37, "witht" should be -- with --
Column 11, line 44, "III" should be -- 111 --.
Column 12, line 23, "produced" should be -- produce --;
　　　　　line 45, "28" should be -- 128 --.
Column 13, line 12, "Thud" should be -- Thus --.

In the Claims:

Claim 3 - change the dependency from "1" to -- 2 --.

Signed and Sealed this

Eighth Day of March 1977

[SEAL]

Attest:

RUTH C. MASON　　　　　　　　C. MARSHALL DANN
Attesting Officer　　　　　　Commissioner of Patents and Trademarks